(12) United States Patent
Stuart-Bruges

(10) Patent No.: US 6,457,357 B1
(45) Date of Patent: Oct. 1, 2002

(54) FLUID DENSITY MEASUREMENT DEVICE

(75) Inventor: William Peter Stuart-Bruges, Basingstoke (GB)

(73) Assignee: Sondex Limited, Hampshire (GB)

( * ) Notice: Subject to any disclaimer, the term of this patent is extended or adjusted under 35 U.S.C. 154(b) by 0 days.

(21) Appl. No.: 09/600,828
(22) PCT Filed: Jan. 26, 1999
(86) PCT No.: PCT/GB99/00259
§ 371 (c)(1), (2), (4) Date: Sep. 25, 2000
(87) PCT Pub. No.: WO99/37988
PCT Pub. Date: Jul. 29, 1999

(30) Foreign Application Priority Data

Jan. 26, 1998 (GB) ................................. 9801604

(51) Int. Cl.⁷ .................................. G01N 9/16
(52) U.S. Cl. ............................ 73/440; 73/454
(58) Field of Search ................... 73/454, 433, 435, 73/436, 437, 440, 444, 448, 451, 452, 453

(56) References Cited

U.S. PATENT DOCUMENTS

| 1,071,167 A | * | 8/1913 | McDonald | 73/454 |
| 1,898,903 A | * | 2/1933 | Schroder | 73/454 |
| 3,604,272 A | * | 9/1971 | Youngs | 73/454 |
| 3,722,292 A | | 3/1973 | Pietramale | |
| 4,215,574 A | | 8/1980 | Godeux | |
| 4,275,593 A | * | 6/1981 | Thornton-Trump | 73/454 |
| 4,353,253 A | | 10/1982 | Callahan | |
| 4,697,454 A | | 10/1987 | Lu | |
| 4,989,453 A | | 2/1991 | Hiiesalu | |

FOREIGN PATENT DOCUMENTS

| DE | 2 402 400 | 7/1975 |
| GB | 2 015 737 | 9/1979 |
| GB | 1 591 157 | 6/1981 |

* cited by examiner

Primary Examiner—Helen Kwok
(74) Attorney, Agent, or Firm—Flynn, Thiel, Boutell & Tanis, P.C.

(57) ABSTRACT

A fluid density measurement device includes a float (12) and a weight (14), each mounted on links (16) for essentially vertical movement. A crank (22) is mounted above the float and weight and is connected to them, by a float link (24) and a counterweight link (28) to convert the forces from the float and the forces from the weight to rotational forces on the crank acting in opposite directions. The position adopted by the crank will be dependent upon the density of the fluid in which the instrument is immersed. The links (16) are arranged so that a good approximation to straight line motion is obtained at the centre of the float and the weight.

10 Claims, 2 Drawing Sheets

FLUID DENSITY MEASUREMENT DEVICE

BACKGROUND OF THE INVENTION

This invention relates to gravimetric fluid density measurement devices.

Fluid density measurement devices are known which are immersed in the fluid and provide a visual reading of the density of the fluid. An example of such a device is described in detail, together with its method of operation, in U.S. Pat. No. 4,353,253. Further devices which can be used for density measurement are described in United Kingdom Patent Specifications 2,015,737 and 1,591,157.

Other devices, also designed for total immersion in the fluid, can be used for remote sensing inside pipelines, oil or water wells, or containers. It is desirable that such devices are made so that they can pass freely through apertures of small diameter, yet, in a non-homogeneous fluid, make readings based on a reasonable displacement volume of fluid.

Devices in common use have suffered from sensitivity to the inclination of the device relative to the vertical, to local gravity effects, and, where the instrument has to be read while moving, to axial acceleration effects.

German Patent Specification DE-A-24 02 400 describes a fluid density measurement device constructed similarly to a balance and which is designed for use above the fluid the density of which is to be measured. United Kingdom Specification GB-A-1,591,157 describes a device for indicating changes in specific gravity of liquid fuel which has two floats and a potentiometer arrangement.

SUMMARY OF THE INVENTION

According to this invention there is provided a fluid density measurement device, comprising a buoyancy element mounted for up and down movement about an axis of movement of the device; a weight mounted for up and down movement substantially parallel to the movement of the buoyancy element; a pivotable element mounted for pivotal movement about an axis substantially orthogonal to the movement axis of the device; a first link coupling the buoyancy element to a first location on the pivotable element to convert axial forces on the buoyancy element to rotary forces on the pivotable element tending to rotate the pivotable element; a second link coupling the weight to a second location on the pivotable element to convert axial forces on the weight to rotary forces on the pivotable element such as in use to balance the forces due to the buoyancy element; and means enabling the position of the moveable elements to be determined, whereby when the weight and the buoyancy element are immersed in a fluid the density of which is to be measured, the position of the moveable elements is dependent of the fluid density.

In a preferred embodiment of the invention, the weight is of generally hollow configuration and the buoyancy element moves within the weight. The means enabling the position of the moveable elements to be determined enables the position of the pivotable element to be determined, and may comprise an electrical transducer for providing an electrical output signal representative of the position of the moveable elements. The device preferably includes links for mounting the buoyancy element and the weight, the links being generally orthogonal to the movement axis and comprising a top link and a bottom link for each of the buoyancy element and the weight, the two top links extending in a first direction, and the two bottom links extending in a second direction opposite to the first direction.

BRIEF DESCRIPTION OF THE DRAWINGS

The invention will now be described in more detail, by way of example, with reference to the drawings, in which.

DETAILED DESCRIPTION OF THE PREFERRED EMBODIMENT

Figure 1:
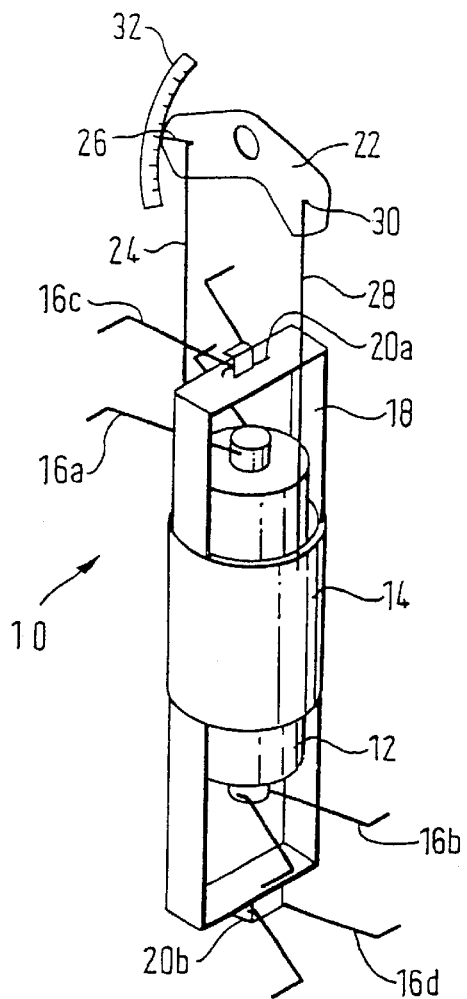
FIG. 1 is a perspective view illustrating the operation of a fluid density measurement device embodying the present invention.

The preferred fluid density measurement device 10 illustrated comprises a float 12 constituting a buoyancy element. The float may be cylindrical in shape about a central main or movement axis and is constructed in any convenient manner. It may conveniently be of plastics material, and may be hollow provided that its volume can be stabilised adequately over the required range of temperature and pressure. A weight 14 is hollow in the form of an annular cylinder and surrounds the float 12. The weight naturally has a density which is much greater than that of the float, and may conveniently be of metal.

The float 12 and the weight 14 are each mounted for axial up and down movement. The terms up and down are used herein with reference to the normal attitude of the device, shown in FIG. 1, though the device is designed to operate over a range of angles of inclination to the vertical, as discussed below. The up and down movement of the float and weight is achieved by means of mounting links 16a to 16d. The top of the float is attached to a generally orthogonal mounting link 16a (horizontal as shown) the other end of which is pivoted to a framework, not shown. The bottom of the float is attached to another generally orthogonal mounting link 16b which is likewise pivoted to the framework, at a lower position than the mounting link 16a. Furthermore in the example shown, the mounting links 16a, 16b extend away from the float in opposed directions. The weight 14, or counterweight, has attached to it a generally rectangular support 18 which extends axially, i.e. in the vertical plane as shown, and provides attachment points 20a and 20b spaced above and below the float. The attachment point 20a is attached to a mounting link 16c which extends in the same direction as the adjacent mounting link 16a to a fixing point on the framework (not shown), and the attachment point 20b is attached to a mounting link 16d which extends in the same direction as the adjacent mounting link 16b to another, lower fixing point on the framework.

In this way the centre of the float and the centre of the weight are constrained for generally axial movement up and down on substantially parallel paths, with the float moving within the hollow weight.

Above the float 12 and the weight 14 a crank 22 is mounted in bearings (not shown) in the framework for pivotal movement about a substantially orthogonal axis to the main axis. The crank is connected to the float and the weight as follows. A float link 24 is attached at its bottom end to the top of the float 12, and at its top end to a first point 26 on the crank 22. The float link transmits axial forces on the float to the crank. The upward buoyancy force or uplift on the float tends to cause the crank to rotate in the clockwise direction as seen in FIG. 1. A counterweight link 28 is attached at its bottom end to an upper point on the weight 14, and at its top end to a second point 30 on the crank 22. The counterweight link 28 transmits the axial forces on the weight to the crank 22. The first and second points 26 and 30 where the links are attached to the crank are spaced, relative to the pivot point of the crank, by about 130°. They may be spaced by other angles between 45° and 180°, depending upon the relative masses of the float and the weight, and on the sensitivity required.

The instrument illustrated is designed for use at very high pressures, for example greater than 10,000 psi (pounds per square inch) or 70 MPa (mega Pascals). To be sufficiently strong the floats are therefore generally denser than the fluids to be measured. In addition, the device may be used to measure very low densities, e.g. of air or gas, where again the float will be denser than the fluid to be measured. The result of this is that the "float" provides a net downwards force on the crank in the embodiment described. In other circumstances, for instance, the weight might tend to rotate the crank in either direction according to the density being measured.

In the illustrated embodiment, the float and weight have approximately equal mass, so the weight combines with the mass of the float to provide a virtual mass attached halfway between the actual points of attachment to the crank. The more obtuse the angle, the nearer this virtual point is to the crank pivot, and hence the smaller the moment which will oppose the tendency to rotate under buoyancy, and the greater the sensitivity.

If, on the other hand, the float had substantially no mass, then it would provide a net upward force. In that case a smaller weight could be attached at say 90° or less.

Figure 2:
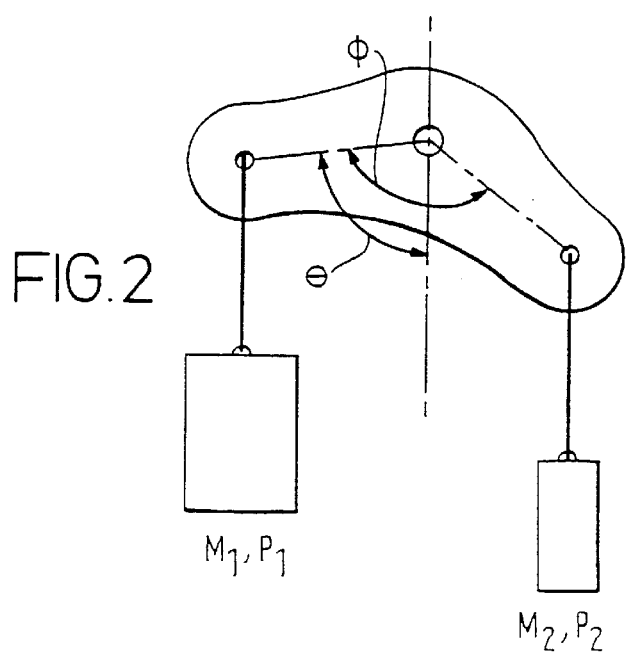
FIG. 2 illustrates the principle of operation of the device of FIG. 1.

The mathematical basis for the illustrated embodiment will now be described with reference to FIG. 2 of the drawings. Consider two elements of mass M1 and M2, densities $\rho_1$ and $\rho_2$, attached via pivoted links to a crank at two points at equal distances from the centre of the crank where the two points subtend an angle $\phi$ at the centre of said crank.

Let the point of attachment of element 1 make an angle $\theta$ with the vertical, the whole system being immersed in fluid of density $\rho$.

Then, for equilibrium:

$$M_1 g \sin\theta - \frac{M_1}{\rho_1} \cdot \rho g \sin\theta = M_2 g \sin(\phi - \theta) - \frac{M_2}{\rho_2} \cdot \rho g \sin(\phi - \theta)$$

$$\rho = \frac{M_2 \sin(\phi - \theta) - M_1 \sin\theta}{\frac{M_2}{\rho_2} \sin(\phi - \theta) - \frac{M_1}{\rho_1} \sin\theta}$$

Thus a response curve relating $\rho$ to $\theta$ may be tabulated for any ratio M1/M2, and any angle $\phi$, and any values of $\rho_1$ and $\rho_2$.

The above analysis presumes that the elements M1 and M2 are always directly below their attachment points on the crank. In a practical device the response will be slightly modified by the variations in link angles as the crank rotates.

If the elements M1 and M2 are constrained to move parallel to the main axis of the instrument, then the response will be independent of the inclination of the axis to the vertical, since all gravitational forces, including buoyancy, will be resolved along that axis.

The float and the weight are constrained to move in straight lines collinear to the axis of the instrument, so that all the forces are resolved on one axis. The crank is effective as an eccentric balance. The mechanism employed to constrain the movements of the float and the counterweight do not have to take the form of the mounting links shown, but could comprise for example sliding guides or rolling guides. The illustrated linkage results in a close approximation to a straight line motion at the centre of the float and the weight, with the advantage that sliding or rolling surfaces are avoided. This can be an advantage when operating in fluids which may contain particles in suspension.

When the device is in use, the float and the weight are immersed in the fluid the density of which is to be measured. The crank 22 will also normally be immersed, though if the fluid is a liquid it can alternatively be above the surface of the liquid. The pivotal or rotary balance position which will be adopted by the crank 22 will depend on the relative magnitude of the force from the float 12 and the force from the weight 14. The position of the crank is therefore dependent upon the density of the fluid. The position of the crank can be read by a user, using a calibrated scale 32 printed on the body of the instrument. Alternatively, a transducer may be mounted adjacent the crank 22 such as to provide an electrical output signal dependent upon the position of the crank.

More particularly, the response of the device will depend upon the density of the float, the relative masses of the float and the counterweight, and the points of connection to the crank. By choosing appropriate mass values and connection geometry, an approximately linear response may be obtained over a range of densities.

As described, the measurement is made by noting or sensing the position of the crank. However, the measurement may alternatively by made by noting or measuring the position of any of the moveable elements, particularly the float or the weight.

The device is designed so as to work over a range of angles of inclination to the vertical (or horizontal). The range of inclination over which the instrument can be used will depend upon the quality of the pivot bearings.

Figure 3:
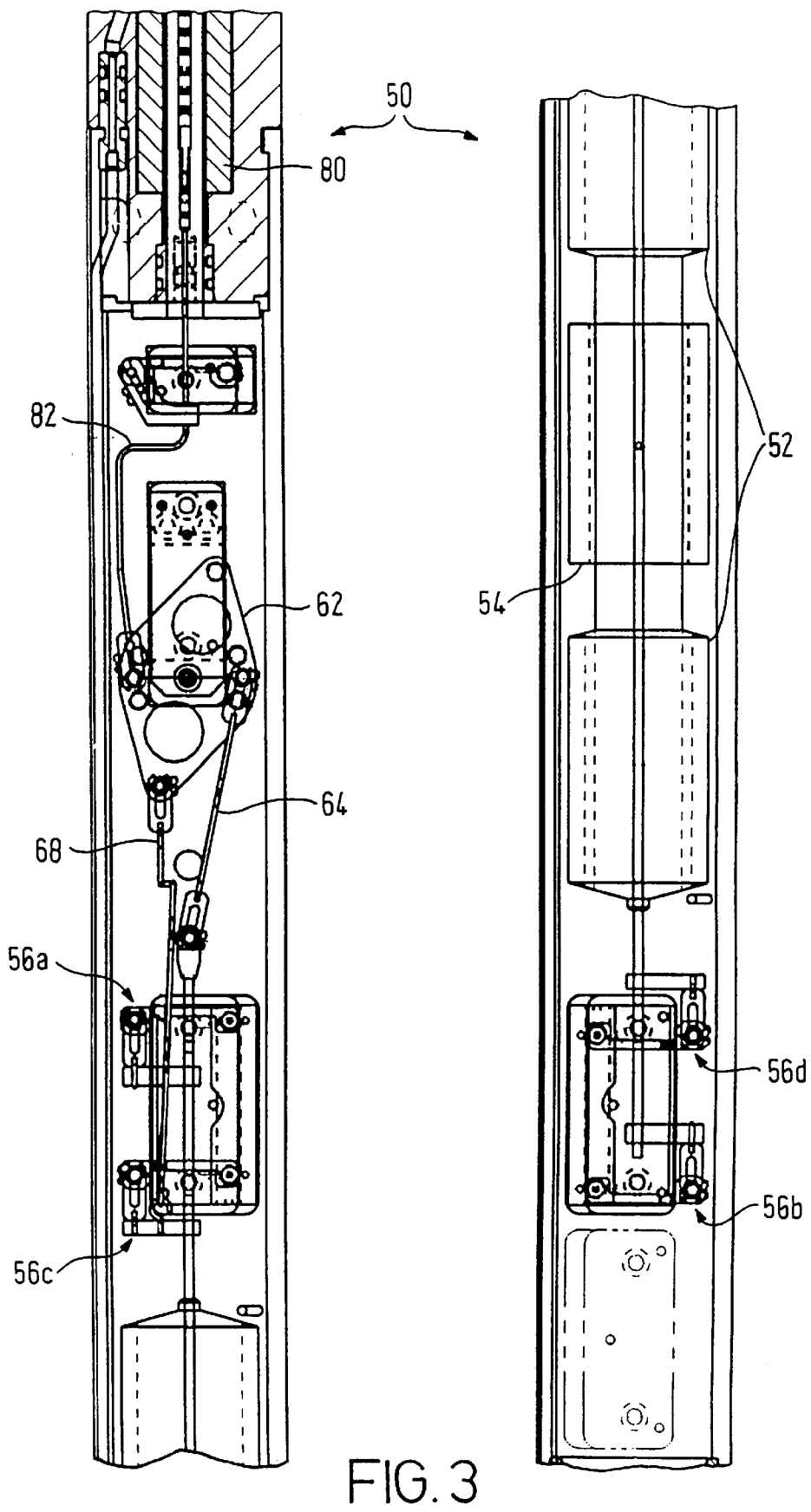
FIG. 3 shows a practical embodiment using the principles of FIG. 1.

FIG. 3 shows a practical implementation of the device. The Figure is in two parts for clarity. The fluid density measurement device 50 shown in FIG. 3 has a float 52 and a weight 54, each mounted for extra up and down movement by means of mounting links 56a to 56d. In this example the mounting links extend away from the float and weight in the same direction, namely to the right as seen in FIG. 3. The crank of FIG. 1 takes the form of a pivoted plate 62 in FIG. 3 and a float link 64 and a counterweight link 68 couple the plate 62 to the float and the counterweight respectively. The plate 62 is connected to an LVDT (linear variable differential transformer) 80 as a measurement device by means of a link 82. Other details will be apparent to those skilled in the art from the drawing.

The instruments illustrated can measure the density of liquids or gases, and can operate in a confined space, such as within vertical and deviated pipelines. The instruments can be designed so that they can be fully immersed in the measured fluid at any normal pressure, and give consistent readings independent of inclination, local gravity, and any accelerations which may occur for instance as the device is moved along a pipeline.

What is claimed is:

1. A fluid density measurement device, comprising:
   a buoyancy element suitable for immersion in a fluid the density of which is to be measured;
   mounting means for the buoyancy element arranged to constrain the movement of the buoyancy element up and down about an axis of movement of the device;
   a weight suitable for immersion in the fluid the density of which is to be measured;

mounting means for the weight arranged to constrain the movement of the weight up and down substantially parallel to the movement of the buoyancy element;

a pivotable element mounted for pivotal movement about an axis substantially orthogonal to the movement axis of the device;

a first link coupling the buoyancy element to a first location on the pivotable element to convert axial forces on the buoyancy element to rotary forces on the pivotable element tending to rotate the pivotable element;

a second link coupling the weight to a second location on the pivotable element to convert axial forces on the weight to rotary forces on the pivotable element in order to, in use, balance the forces due to the buoyancy element, said buoyancy element, weight, pivotable element and first and second links defining movable elements of said fluid density measurement device; and means for enabling a position of the moveable elements to be determined, whereby when the weight and the buoyancy element are immersed in the fluid the density of which is to be measured, the position of the moveable elements is dependent of the fluid density.

2. A fluid density measurement device according to claim 1, in which the weight is of generally hollow configuration and the buoyancy element moves within the weight.

3. A fluid density measurement device according to claim 1, in which the means for enabling the position of the moveable elements to be determined enables a position of the pivotable element to be determined.

4. A fluid density measurement device according to claim 1, in which the means for enabling the position of the moveable elements to be determined comprises an electrical transducer for providing an electrical output signal representative of the position of the moveable elements.

5. A fluid density measurement device according to claim 1, in which the mounting means for the buoyancy element and the weight comprise a plurality of links, the links being generally orthogonal to the movement axis and comprising a top link and a bottom link for each of the buoyancy element and the weight, the two top links extending in a first direction, and the two bottom links extending in a second direction opposite to the first direction.

6. A method of measuring the density of a fluid, the method comprising the steps of:

providing an apparatus which comprises a buoyancy element suitable for immersion in a fluid the density of which is to be measured, mounting means for the buoyancy element arranged to constrain the movement of the buoyancy element up and down about an axis of movement of the device, a weight suitable for immersion in the fluid the density of which is to be measured, mounting means for the weight arranged to constrain the movement of the weight up and down substantially parallel to the movement of the buoyancy element, a pivotable element mounted for pivotal movement about an axis substantially orthogonal to the movement axis of the device, a first link coupling the buoyancy element to-a first location on the pivotable element to convert axial forces on the buoyancy element to rotary forces on the pivotable element tending to rotate the pivotable element, a second link coupling the weight to a second location on the pivotable element to convert axial forces on the weight to rotary forces on the pivotable element in order to, in use, balance the forces due to the buoyancy element, said buoyancy element, weight, pivotable element and first and second links defining moveable elements, and said apparatus further comprising means for enabling a position of the moveable elements to be determined;

immersing the weight and the buoyancy element in the fluid the density of which is to be measured; and detecting the position of the moveable elements to determine a measure of the density of the fluid.

7. A method. according to claim 6, wherein the weight has a hollow configuration, said method further including the steps of providing the buoyancy element within and allowing the buoyancy element to move within said weight.

8. A method according to claim 6, wherein the step of detecting the position of the movable elements includes the step of determining a position of the pivotable element to determine the density of the fluid.

9. A method according to claim 6, wherein the means for enabling the position of the movable elements to be determined comprises an electrical transducer, said method including the step of providing an electrical output signal from said transducer which is representative of the position of the movable elements.

10. A method according to claim 6, wherein the mounting means for the buoyancy element and the weight comprise a plurality of mounting links, the mounting links being generally orthogonal to the movement axis and comprising a top mounting link and a bottom mounting link for each of the buoyancy element and the weight, the two top mounting links extending in a first direction, and the two bottom mounting links extending in a second direction opposite to the first direction.

* * * * *